United States Patent [19]

Roberts et al.

[11] Patent Number: 5,372,583

[45] Date of Patent: Dec. 13, 1994

[54] BONE MARROW INFUSER AND METHOD OF USE

[75] Inventors: Craig P. Roberts, San Marcos; Frank J. McManus, Escondido; Ken Litzie, Irvine, all of Calif.

[73] Assignee: Cardiopulmonary Specialities, Inc., Irvine, Calif.

[21] Appl. No.: 981,794

[22] Filed: Nov. 25, 1992

[51] Int. Cl.$^5$ .............................................. A61M 25/00
[52] U.S. Cl. ........................................ 604/51; 604/93; 604/175; 604/264; 128/754
[58] Field of Search ................. 604/51, 93, 174–175, 604/264, 272, 274; 128/754; 606/79–80

[56] References Cited

U.S. PATENT DOCUMENTS

| | | | |
|---|---|---|---|
| 3,540,451 | 11/1978 | Zeman | 604/175 X |
| 4,142,517 | 3/1979 | Stavropoulos et al. | 606/79 X |
| 4,491,126 | 1/1985 | Cullor | 604/175 X |
| 4,772,261 | 9/1988 | Von Hoff et al. | 604/51 |
| 4,782,833 | 11/1988 | Einhorn et al. | 606/80 |
| 5,120,312 | 1/1992 | Wigness et al. | 604/175 |
| 5,122,114 | 6/1992 | Miller et al. | 604/49 |
| 5,192,282 | 3/1993 | Draenert | 606/65 |

FOREIGN PATENT DOCUMENTS 1315796 5/1973 United Kingdom ............... 604/273

OTHER PUBLICATIONS

D. Von Hoff, "Intraosseous Infusions: An Important But Forgotten Method of Vascular Access", *Cancer Investigation*, 9(5), p. 524 (1991).
D. Driggers, et al., "Emergency Resuscitation In Children: The Role of Intraosseous Infusion", *Emergency Resuscitation*, vol. 89, No. 4, p. 129 (Mar. 1991).
"Modern Health Care Technology", *Journal of Intravenous Nursing*, vol. 12, No. 6, p. 371.
D. Fiser, "Intraosseus Infusion", *New England Journal of Medicine*, vol. 322, No. 22, p. 1579 (May 31, 1990).
L. Halvorsen, et al., "Evaluation of an Intraosseous Infusion Device for the Resuscitation of Hypovolemic Shock", *Journal of Trauma*, vol. 30, No. 6, p. 652 (Jun. 1990).
Baxter, "Pharma Seal Jamshidi and Illinois Sternal-/Iliac Bone Marrow Biopsy/Aspiration Needles", (advertisement), 1991).

Primary Examiner—C. Fred Rosenbaum
Assistant Examiner—Corrine Maglione
Attorney, Agent, or Firm—Charles H. Schwartz; Ellsworth R. Roston

[57] ABSTRACT

A bone marrow infuser has an intraosseous cannula, a hand driver, and a pointed stylet attached to the hand driver. The hand driver can mechanically couple with the intraosseous cannula so that the stylet point protrudes from an opening at the end of the intraosseous cannula. A method of bone marrow infusion has a first step of puncturing the skin with the point of the stylet, a second step of embedding the cannula into the bone, a third step of removing the stylet from the cannula and attaching the catheter to the cannula, a fourth step of applying pressure to compress the skin, flesh, and bone, and a final step of infusing fluids into the bone marrow.

23 Claims, 2 Drawing Sheets

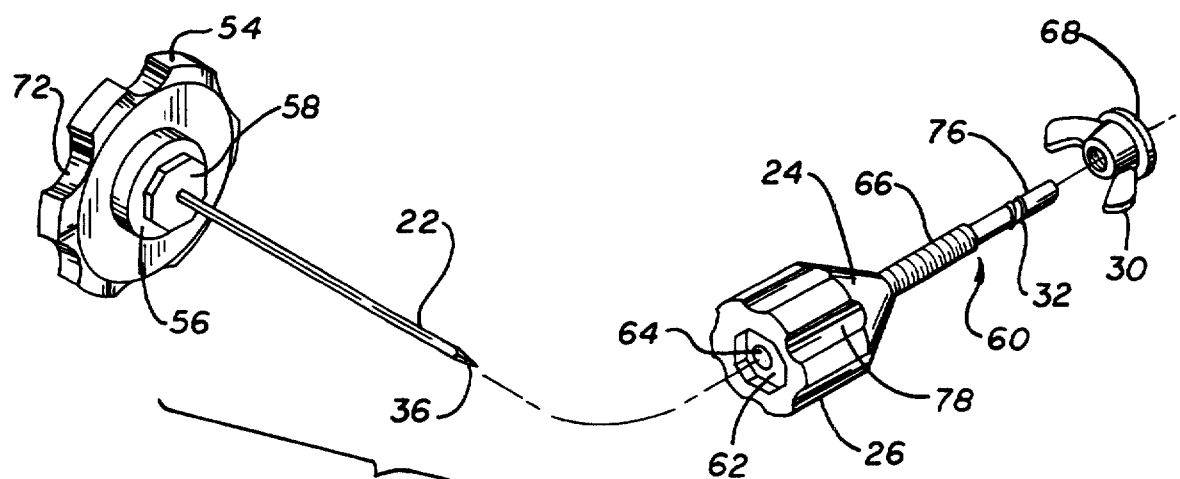
FIG. 3
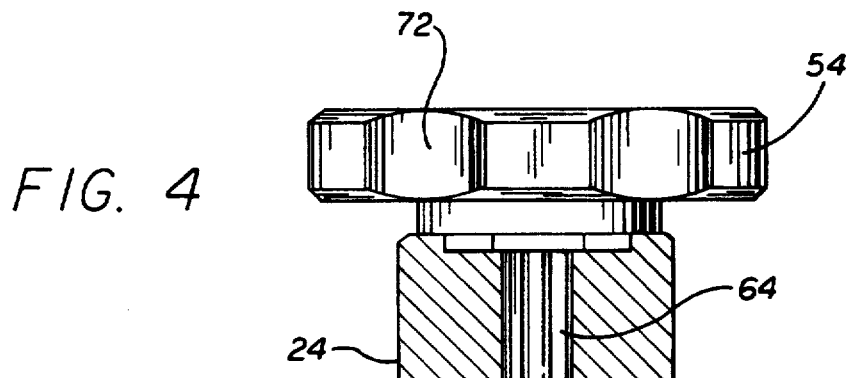
FIG. 4
FIG. 5
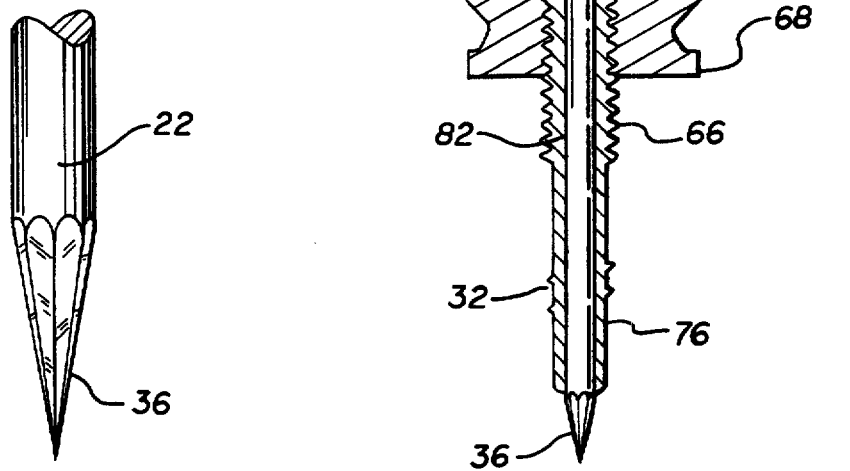

BONE MARROW INFUSER AND METHOD OF USE

FIELD OF THE INVENTION

This invention relates to intraosseus bone marrow medication infusing devices.

BACKGROUND OF THE INVENTION

In many medical emergencies, medical personnel must gain rapid access to the body's vascular system in order to replace fluids and administer medication. This is typically accomplished by attaching a needle to a catheter or syringe, inserting the needle into a vein, and injecting the medical fluids into the bloodstream. However, finding a suitable vein in an emergency can be difficult and time-consuming. For instance, infants and small children may have veins that are barely visible and hard to find. Other problems arise when the patient is an I.V. drug user, and in cases of cardiac arrest, shock, extensive burns, and the like.

Fortunately, access to the vascular system can also be obtained through the bones. With a technique known as intraosseus infusion, an injection device is inserted into the interior of a bone, such as the tibia. Medical fluids are then injected directly into the bone marrow. The fluids flow through the rich vascular network of which the bone marrow is a part, and into the rest of the body.

Although there are a number of existing approaches to intraosseus infusion, the prior known arrangements have significant shortcomings. "Intraosseous Infusions: An Important But Forgotten Method of Vascular Access," by D. D. Von Hoff (*Cancer Investigation*, 9(5), p. 524 (1991)), suggests an approach using a device that is surgically implanted into the bone. To implant the device, a doctor first cuts through the skin, then drills a pilot hole into the bone, and finally screws the device into the bone at the pilot hole. A needle on the end of intravenous tubing or a syringe is then inserted through the skin into the device. Unfortunately, this surgical approach is poorly suited for use in emergency situations, where time is short and a doctor may not be available.

A simpler method is reported in two other articles, "Emergency Resuscitation In Children: The Role of Intraosseus Infusion," by D. A. Driggers, et al., (*Emergency Resuscitation*, Vol. 89, No. 4, p. 129 (March 1991)) and "Pediatric Intraosseous Infusion: An Old Technique in Modern Health Care Technology," by C. A. Wheeler (*Journal of Intravenous Nursing*, Vol. 12, No. 6, p. 371), by which a needle is directly inserted into the bone marrow. Two problems are apparent when this method is used with ordinary medical needles. First, the flexibility of many needles prevents them from penetrating the bone, or at least makes them very difficult to work with. Secondly, the opening at the end of a typical needle is likely to become plugged with bone fragments during insertion, thereby blocking the flow of fluid into the marrow.

Problems arise even when special bone marrow needles are used, such as those disclosed in the Baxter advertisement entitled, "Pharmaseal® Jamshidi® and Illinois Sternal/Iliac Bone Marrow Biopsy/Aspiration Needles," and discussed in "Intraosseous Infusion" by D. H. Fiser (*New England Journal of Medicine*, Vol. 322, No. 22, p. 1579 (May 31, 1990)). Those needles consist of a narrow shaft and a slightly longer stylet with an off-center point at the end. Unfortunately, the needles do not anchor into the bone upon insertion and can be pulled out by accident. Additionally, when a technician rotates the needle to penetrate the bone, the off-center point may cause injury to the overlying skin, muscle, and other tissue of the patient. It should also be noted that none of these needles apply pressure to the skin at the puncture site, and these two negative factors mean that bleeding from the insertion point is likely to occur.

"Evaluation of an Intraosseous Infusion Device for the Resuscitation of Hypovolemic Shock," by L. Halvorsen, et al. (*Journal of Trauma*, Vol. 30, No. 6, p. 652 (June 1990)), describes a device which includes a shaft with a sharp threaded tip, a knob to rotate the shaft, and a spring mechanism to apply pressure to the skin. A medical technician rotates the shaft tip through the bone and into the marrow. It appears from the Halvorsen drawing and text that medical fluids are infused into the bone marrow through an opening in the sharp tip. A number of drawbacks are apparent in the Halvorsen device. First, the opening in the tip can become clogged during entry into the bone. Second, the narrow diameter of the knob does not appear to be well-suited to generating sufficient torque for easy penetration of the dense outer portion of the bone. Third, the pressure on the skin and flesh generated by the spring cannot be adjusted, which may result in either too much pressure or not enough, depending on variable factors such as the depth of penetration, for example. Additionally, once the threaded tip has fully entered the soft bone marrow, as illustrated in FIG. 2 of the Halvorsen article, there is nothing to securely anchor the device in place.

SUMMARY OF THE INVENTION

It is desirable to create a bone marrow infusion device that can be quickly and reliably installed by a variety of medical personnel. The device should not clog during insertion and should anchor itself securely into the bone so that it is not easily displaced. Furthermore, the device should provide pressure on the skin at the point of penetration, but this should be accomplished in an adjustable manner. These goals are satisfied by the device and method of the present invention.

The device itself is a bone marrow infuser having a driver with an extended, pointed stylet for penetrating the hard outer calceous shell of a bone. The driver has a large diameter upper portion with an irregular outer surface for convenient gripping by a doctor or medical professional. The bone marrow infuser also has a medication-feeding cannula with a central channel closely fitting around the extended, pointed stylet. The driver can mechanically couple with the cannula for concurrent rotation, with the cannula being slightly shorter than the pointed stylet when they are coupled together. The cannula has sharp screw threads on its outer surface for the purpose of securing the cannula into the hard outer shell of the bone, such that the inner end of the cannula extends beyond the outer shell of the bone and into the marrow. The outer portion of the cannula has a port that receives medication and transmits it to the interior of the bone, once the driver has been decoupled from the cannula.

In accordance with an additional feature of the invention, the cannula may include a middle portion with a set of threads, preferably standard machine-type threads. A nut engages with the threads and travels linearly along the threads when rotated. The nut is preferably a wing nut which can be rotated to apply light pressure to a bandage overlying a patient's skin.

In accordance with a collateral feature of the invention, the point of the stylet may be multi-faceted, to assist in penetration of the bone.

A preferred method of intraosseous infusion comprises the following steps. A medical technician first punctures the skin with the sharp point of the stylet, which protrudes from the end of the cannula. The technician then rotates the stylet while applying inward pressure to the driver, to penetrate the outer hard surface of the bone; and then embeds the self-tapping threads of the cannula into the bone such that the terminal end of the cannula extends into the bone marrow. The technician removes the stylet, attaches a catheter to the cannula, and rotates the nut down onto a bandage at the surface of the skin in order to limit bleeding. Fluids are then infused directly into the bone marrow.

As is apparent from the description of the bone marrow infuser and the associated method of use, the goals of the invention are readily satisfied. The device can be quickly installed by any medical technician who has sufficient training and practice. The device does not clog during insertion because the stylet prevents matter from entering into the cannula. The device is not easily displaced because it is embedded into the bone. Additionally, rotation of the nut provides pressure on the skin, but the pressure and its point of application along the length of the cannula can be adjusted by further rotation of the nut.

It is noted in passing that the flow of medication into the circulatory system, when medication is supplied to the marrow or intramedullary portion of the bones, is comparable to the flow of medication introduced directly into a vein. Accordingly, the present reliable intraosseous infuser, which overcomes the problems of prior such devices, has an immediate application for many situations as discussed above where venous cannulation is not easily accomplished.

Other objects, features, and advantages of the invention will become apparent from the consideration of the following detailed description and from the accompanying drawings.

BRIEF DESCRIPTION OF THE DRAWING

FIG. 3 is an exploded perspective view showing the hand driver, stylet, and the intraosseus cannula of FIG. 1;

FIG. 4 is a cross-sectional view of the components of FIG. 3 showing the hand driver and stylet mechanically coupled with the intraosseus cannula; and FIG. 5 is a fragmentary enlarged view of a preferred version of the stylet point.

DETAILED DESCRIPTION OF THE PREFERRED EMBODIMENT

Figure 1:
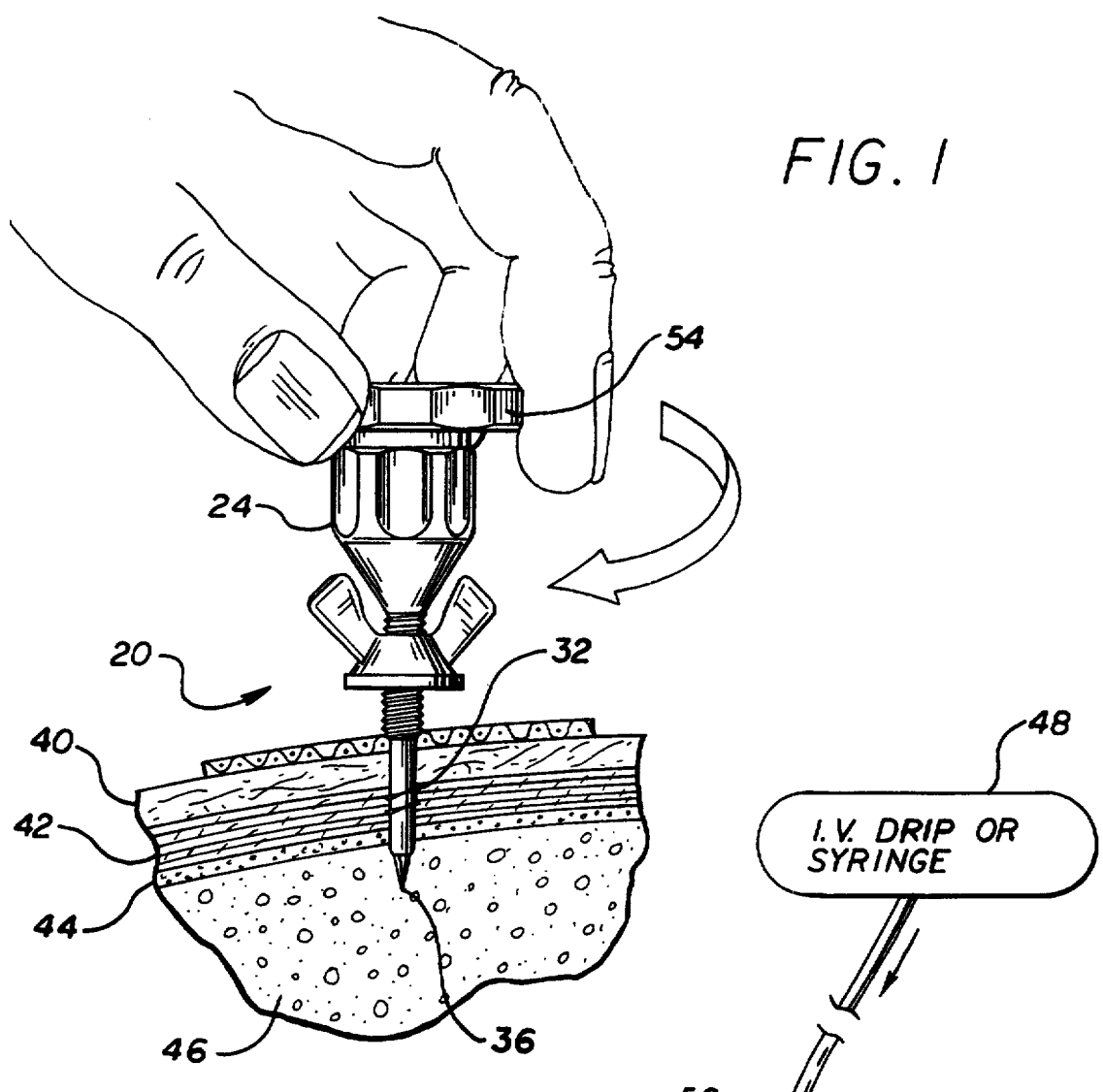
FIG. 1 is a side view showing a user inserting a preferred embodiment of the bone marrow infuser into the bone marrow.

Referring now to the drawings, FIG. 1 illustrates a medical technician positioning the bone marrow infuser 20. After application of a local anesthetic, the technician applies firm downward pressure to hand driver 54 while simultaneously rotating the hand driver in a back and forth rotary motion. The downward pressure and rotary motion cause sharp point 36 to penetrate through the skin 40, the subcutaneous tissue 42, the dense outer layer of bone 44, and finally, into the bone marrow 46. Hand driver 54 has a wide diameter relative to that of intraosseus cannula 24, thereby providing additional torque for ease of entry into the bone.

Figure 2:
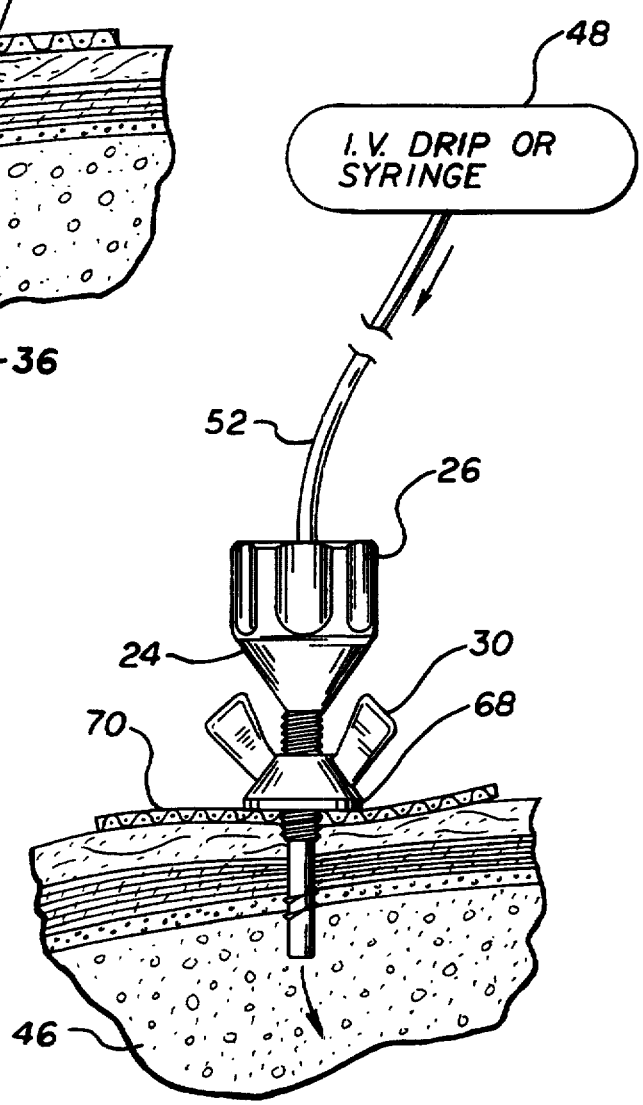
FIG. 2 is a side view showing the bone marrow infuser of FIG. 1 in place and connected to an I.V. drip or syringe via a catheter.

FIG. 2 shows the bone marrow infuser 20 fully in place and providing medical fluids to the bone marrow. Wing nut 30 has been advanced to engage washer 68 and bandage 70 to form a localized "compression bandage" at the site of the puncture. The hand driver 54 and stylet 22 [see FIG. 3] have been disengaged from intraosseus cannula 24. Fitting 26 of intraosseus cannula 24 acts as a port for catheter 52. An I.V. drip or syringe 48 supplies fluids which flow first through catheter 52, then through intraosseus cannula 24, and ultimately into bone marrow 46. The localized "compression bandage" minimizes skin, periosteal, and bone leakage of the fluids.

FIG. 3 is an exploded perspective view showing all of the components of the bone marrow infuser 20. Hand driver 54 is shown at the left side of FIG. 3 having handle indentations 72 which enable the user to obtain a firm grasp when rotating the infuser. Cylindrical protrusion 56, polygonal protrusion 58, and stylet 22 are either machined out of the same piece of material as, or are rigidly attached to, hand driver 54. Stylet 22 includes a sharp, multi-faceted point 36.

Intraosseus cannula 24 includes fitting 26 and a tubular portion 60. Fitting 26 includes a polygonal recess 62, indentations 78 for firm grip, and catheter port 64. The exterior of tubular portion 60 includes standard machine-type threads 66, self-tapping threads 32, and a smooth, tapered end 76. Wing nut 30 engages with machine threads 66 and travels linearly along the threads when rotated. Washer 68 may be fixedly attached to wing nut 30.

Stylet 22 fits through catheter port 64 and mates with the lumen or central opening 82 (FIG. 4) of the tubular portion 60 of intraosseus cannula 24. Polygonal recess 62 is the female counterpart to polygonal protrusion 58 on hand driver 54, so that rotation of the driver 54 rotates the cannula 24. The tip 76 of the cannula is slightly tapered to ensure a snug fit when mated with stylet 22.

FIG. 4 shows hand driver 54 and stylet 22 mated with intraosseus cannula 24, as the device would appear during insertion into the bone marrow. Hand driver 54 is mechanically interconnected with fitting 26 such that cannula 24 rotates whenever hand driver 54 is rotated. In this embodiment of the invention, catheter port 64 has a larger diameter than cannula lumen 82 to receive medication dispensing tube 52 and to prevent the tube 52 from entering cannula lumen 82. Note that the snug fit between the stylet 22 and the cannula 24 prevents pieces of bone from clogging the cannula during insertion.

FIG. 5 is a fragmentary enlarged view of the multi-faceted sharp point 36 of stylet 22. Note that the sharp point 36 is located along the central axis of stylet 22. This advantageous positioning minimizes the amount of skin, flesh, and bone that the point cuts as it passes to the marrow.

The preferred method of installing and utilizing the device is as follows. The stylet 22 and hand driver 54 are mated with intraosseus cannula 24 as in FIG. 4. A medical technician selects a site for insertion, then aseptically prepares the skin. If the patient is conscious, the technician also anesthetizes the skin and periosteum. The technician then positions the stylet tip 36 on the insertion site and applies firm pressure and a rotary motion causing tip 76 of the cannula 24 to advance through the skin 40, subcutaneous tissue 42, and outer layer of the bone 44. Once resistance to the advancing cannula decreases, the technician rotates the hand driver 54 at least one full rotation to embed self-tapping threads 32 into the dense outer portion of the bone 44. The stylet is then removed and proper positioning of the device is verified by aspiration of blood and marrow contents. Infusion of fluids may begin after the cannula is flushed with saline. The technician may rotate wing nut 30 to adjustably compress bandage 20 to the skin 40 at the site of insertion.

The bone marrow infuser can be provided in a variety of sizes to meet the varying needs of infants, children, senior citizens, tall people, and so on. Exemplary dimensions for a few of these sizes are as follows. Intraosseous cannula 24 may be between 4 and 10 cm. in length. The distal 5-7 mm. has a smooth outer diameter which may taper slightly at the terminal end. The next 3-5 mm. has self-tapping threads 32 designed to anchor the cannula into the dense outer portion of the bone. The remaining length of the cannula is threaded with threads 66, which are preferably standard machine-type threads, to accommodate a wing nut 30 and skin compression washer 68. The lumen of the cannula 82 should have a diameter of between ½ and 5 mm., so as to facilitate substantial volume flow, and catheter port 64 may have a diameter of between 3 and 7 mm. The hand driver 54 may have an outer diameter of between 2 and 3½ cm., and the fitting 26 of the cannula may have an outer diameter of between 1 and 2½ cm.

In conclusion, it is to be understood that the foregoing detailed description and the accompanying drawings relate to a preferred embodiment of the invention. Various changes and modifications may be made without departing from the spirit and scope of the invention. Thus, by way of example and not of limitation, the hand driver 54 need not be round but could be square or triangular, or could simply be a flange. Hand driver 54 could also be extended in length, like the handle of a screw driver. Protrusion 58 and recess 62 could be of a variety of shapes, including square or star shaped. A number of other mechanical arrangements could be used for coupling the hand driver 54 with fitting 26, such as interlocking pins. Wing nut 30 and washer 68 could be replaced by a single, threaded disk. In addition, stylet point 36 could have more or fewer facets, or could even be without facets entirely. Instead of a wing nut and mating threads, a sliding member having frictional engagement with the outer surface of the cannula, may be employed to apply light pressure to the bandage around the puncture point. Accordingly, the present invention is not limited to the specific embodiments shown in the drawings and described in the detailed description.

What is claimed is:

1. A method of intraosseous infusion utilizing a cannula having self-tapping threads, a removable stylet having a sharp point for insertion through the cannula, a hand driver coupled to the cannula and removable stylet, and a nut rotatable engaging a portion of the cannula, comprising the steps of:

puncturing skin with a sharp point of a stylet which protrudes from an end of a cannula;

embedding the self-tapping threads of the cannula into bone such that the terminal end of the cannula extends into bone marrow;

removing the stylet from the cannula;

attaching a medication supplying tube or catheter to the cannula;

compressing a bandage onto the skin above the bone by rotating the nut to reduce bleeding; and infusing the bone marrow with fluids.

2. The method of claim 1, wherein the step of compressing a bandage onto the skin above the bone by rotating the nut includes mounting a wing nut and a washer on the cannula and rotating the wing nut.

3. The method of claim 2, wherein the step of compressing skin and flesh above the bone also includes placing a bandage underneath the wing nut and washer before rotating the wing nut.

4. The method of claim 1, wherein the step of embedding the self-tapping threads of the cannula into the bone includes applying firm pressure and a rotary motion to the device, then rotating the cannula until said self-tapping threads are embedded into the outer hard shell of the bone and an end of the cannula protrudes into bone marrow.

5. The method of claim 1, wherein the step of infusing bone marrow with fluids includes causing fluids to flow from an I.V. drip or syringe, through the cannula, and into the bone marrow.

6. A bone marrow infuser comprising:

an intraosseous cannula including a proximal end having a fitting, a middle portion having a first set of threads, a distal end having self-tapping threads, and a lumen;

a hand driver;

a stylet fixedly attached to the hand driver at one end and including a sharp point at the opposite end;

means for mechanically coupling said hand driver with said intraosseous cannula so that the cannula and stylet can be rotated at the same time by the hand driver;

said cannula having an opening at the distal end such that the sharp point of said stylet protrudes from said opening when the hand driver is mechanically coupled to the intraosseous cannula; and a nut which engages with said first set of threads on said intraosseous cannula;

whereby said infuser may penetrate the outer hard outer shell of the bone and the cannula is secured thereto by rotation of the hand driver and engagement of the self-taping threads, and medication infusion may be started following removal of the hand driver and stylet.

7. The bone marrow infuser as defined in claim 6, wherein said means for mechanically coupling said hand driver with said intraosseous cannula includes a polygonal protrusion on one of either the driver or the cannula and a mating polygonal recess on the other.

8. The bone marrow infuser as defined in claim 6, wherein said hand driver is of a generally circular shape having indentations around the perimeter, said hand driver having a diameter greater than that of said fitting of said intraosseous cannula.

9. The bone marrow infuser as defined in claim 6, wherein said nut is a wing nut which can be rotated to apply light pressure surrounding said infuser between said nut and the hard outer shell of the bone.

10. The bone marrow infuser as defined in claim 6, wherein said distal end of said intraosseous cannula is tapered for a snug fit with said stylet.

11. The bone marrow infuser as defined in claim 6, wherein said point of said stylet is located along the central axis of said stylet.

12. The bone marrow infuser as defined in claim 6, wherein said first set of threads of said middle portion of said intraosseous cannula are standard machine-type threads.

13. The bone marrow infuser as defined in claim 6, wherein said fitting on said intraosseous cannula includes means to connect said fitting to a tube for supplying medication, said means comprising a bore that is shorter than and coaxial to said lumen, said bore having diameter equal to or greater than said lumen.

14. The bone marrow infuser as defined in claim 6, wherein said self-tapping threads on said distal end of said cannula are set back from said opening at said distal end such that a portion of said distal end, including said opening, protrudes into bone marrow when said self-tapping threads are secured into the outer hard shell of the bone.

15. An intraosseous penetrating, securing, and medication supplying apparatus, comprising:
- a driver including an extended pointed member having means for penetrating the hard outer calceous shell of a bone, said driver having a large diameter portion having an outer irregular surface for convenience gripping by a doctor or medical professional;
- a hollow intraosseous medication feeding cannula, said cannula having a central channel closely fitting around said extended pointed member and with said driver, including said extended pointed member, being removable from said cannula;
- means associated with said driver and said cannula for mechanically coupling them together for concurrent rotation of said extended pointed member and said cannula and wherein said means for mechanically coupling said driver and said cannula comprises a polygonal protrusion on said driver and a mating polygonal recess in said cannula;
- said cannula being slightly shorter than said pointed member of said driver when they are coupled together;
- said cannula having sharp screw threads on the outer surface thereof to secure said feeding member into the outer hard shell of the bone with the inner end of said feeding member extending into the intramedullary region of said bone; and
- the outer portion of said cannula having a port for receiving medication and supplying it within the bone, following removal of the driver and said extended pointed member.

16. The intraosseous apparatus as defined in claim 15, wherein said cannula includes means for providing adjustable pressure on skin, subcutaneous tissue, and bone when said cannula is secured into said outer hard shell of said bone.

17. The intraosseous apparatus as defined in claim 16, wherein said means for providing adjustable pressure on skin, subcutaneous tissue, and bone when said cannula is secured into said outer hard shell of said bone comprises standard machine-type threads on the outer surface of said cannula and a wing nut which engages with said standard machine threads, whereby said wing nut travels linearly along said standard machine threads when said wing nut is rotated.

18. The intraosseous penetrator as defined in claim 15, wherein said extended pointed member includes a central axis and a sharp point located along said central axis.

19. The intraosseous penetrator as defined in claim 15, wherein said outer irregular surface of said large diameter upper portion of said driver is of a generally circular shape having indentations around the perimeter thereof.

20. An intraosseous penetrating, securing, and medication supplying apparatus, comprising:
- a driver including an extended pointed member having means for penetrating the hard outer calceous shell of a bone, said driver having a large diameter portion having an outer irregular surface for convenience gripping by a doctor or medical professional and wherein said extended pointed member includes a central axis and a sharp point located along said central axis;
- a hollow intraosseous medication feeding cannula, said cannula having a central channel closely fitting around said extended pointed member and with said driver, including said extended pointed member, being removable from said cannula;
- means associated with said driver and said cannula for mechanically coupling them together for concurrent rotation of said extended pointed member and said cannula;
- said cannula being slightly shorter than said pointed member of said driver when they are coupled together;
- said cannula having sharp screw threads on the outer surface thereof to secure said feeding member into the outer hard shell of the bone with the inner end of said feeding member extending into the intramedullary region of said bone; and
- the outer portion of said cannula having a port for receiving medication and supplying it within the bone, following removal of the driver and said extended pointed member.

21. The intraosseous apparatus as defined in claim 20, wherein said cannula includes means for providing adjustable pressure on skin, subcutaneous tissue, and bone when said cannula is secured into said outer hard shall of said bone.

22. The intraosseous apparatus as defined in claim 21, wherein said means for providing adjustable pressure on skin, subcutaneous tissue, and bone when said cannula is secured into said outer hard shell of said bone comprises standard machine-type threads on the outer surface of said cannula and a wing nut which engages with said standard machine threads, whereby said wing nut travels linearly along said standard machine threads when said wing nut is rotated.

23. The intraosseous penetrator as defined in claim 20, wherein said outer irregular surface of said large diameter upper portion of said driver is of a generally circular shape having indentations around the perimeter thereof.

* * * * *